US010105347B2

(12) United States Patent
Gokaraju et al.

(10) Patent No.: US 10,105,347 B2
(45) Date of Patent: Oct. 23, 2018

(54) SPHAERANTHUS INDICUS DERIVED INGREDIENTS AND THEIR COMPOSITIONS FOR ENHANCING PHYSICAL PERFORMANCE AND ENERGY LEVELS

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Kiran Bhupathiraju, Vijayawada (IN); Venkata Krishna Raju Alluri, Vijayawada (IN)

(73) Assignee: LAILA NUTRACEUTICALS, Vijayawada (IN)

(*) Notice: Subject to any disclaimer, the term of this patent is extended or adjusted under 35 U.S.C. 154(b) by 839 days.

(21) Appl. No.: 13/793,084

(22) Filed: Mar. 11, 2013

(65) Prior Publication Data

US 2013/0189380 A1 Jul. 25, 2013

Related U.S. Application Data

(63) Continuation-in-part of application No. PCT/IN2011/000612, filed on Sep. 7, 2011, and a continuation-in-part of application No. 13/146,965, filed as application No. PCT/IN2010/000053 on Feb. 2, 2009, now Pat. No. 9,241,964.

(30) Foreign Application Priority Data

Feb. 2, 2009 (IN) .............................. 224/CHE/2009
Sep. 11, 2010 (IN) ............................ 2296/CHE/2010

(51) Int. Cl.
*A61K 31/365* (2006.01)
*A61K 31/352* (2006.01)
*A61K 45/06* (2006.01)

(52) U.S. Cl.
CPC .......... *A61K 31/365* (2013.01); *A61K 31/352* (2013.01); *A61K 45/06* (2013.01)

(58) Field of Classification Search
None
See application file for complete search history.

(56) References Cited

U.S. PATENT DOCUMENTS

2006/0057229 A1 3/2006 Inomata et al.
2007/0087108 A1* 4/2007 Wadsworth .............. A23K 1/14
426/635
2007/0122496 A1* 5/2007 Managoli ............. A61K 35/748
424/725
2008/0254157 A1 10/2008 Chauhan et al.

FOREIGN PATENT DOCUMENTS

JP 07138126 A 5/1995
JP 09110688 A 4/1997
WO WO 2006134609 A2 * 12/2006 ............. A61K 36/28

OTHER PUBLICATIONS

Ambavade et al. Indian J Pharmacol. Aug. 2006. vol. 38, Issue 4. 254-259.*
Browning et al. Anesthesia Progress. Mar./Apr. 1987. pp. 46-50.*
Bafna et al. J Herb Pharmacother. 2007;7(1):25-37.*
International Search Report dated Mar. 21, 2012 for WO2012/1032544.
Jadhav et al., Two new eudesmanolides from Sphaeranthus indicus (Linn) Indian J. Chem vol. 46B (2007) pp. 379-381.
Sodḍala Title of publication—Soḍhalanighaṇṭauḥ Page(s) being submitted—5 (p. 4-8) ( Ref. p. No. of publication:106 ) Publication Date—Edn. 1st, 1978 Publisher—Oriental Institute Place of Publication—Baroda, India.†
Govinda Dasa Title of publication—Bhaiṣajya Ratnāval Page(s) being submitted—7 (p. 9-15) (Ref. p. No. of publication:437) Publication Date—Edn. 14th, 2001 Publisher—Chaukhamba Sanskrit Sansthan Place of Publication—Varanasi, India.†
Title of publication—Agnipurāṇama Page(s) being submitted—8 (p. 16-23) (Ref. p. No. of publication:412-413) Publication Date—Ed. 2nd 1998 Publisher—Hindi Sahitya Sammelana Place of Publication—Prayaya, India.†

* cited by examiner
† cited by third party

*Primary Examiner* — Amy L Clark
(74) *Attorney, Agent, or Firm* — Kramer Amado, P.C.

(57) ABSTRACT

The invention discloses herbal ingredients derived from *Sphaeranthus indicus* standardized to at least one frullanolide/eudesmanoid sesquiterpene compound and their compositions as natural energy enhancer to provide an onset and steady maintenance of energy and mental alertness in a mammal. The invention further includes the use of ingredients and compositions for food ingredient formulations such as dietary supplement, food ingredient, beverage, snack or energy drink containing the above said herbal ingredient(s) for enhancing physical activity, physical fitness, mental alertness, enhancing energy levels, stamina levels, circulatory health, blood vessel health and for better mental health in warm blooded animal.

17 Claims, 4 Drawing Sheets

SPHAERANTHUS INDICUS DERIVED INGREDIENTS AND THEIR COMPOSITIONS FOR ENHANCING PHYSICAL PERFORMANCE AND ENERGY LEVELS

CROSS-REFERENCE TO RELATED APPLICATIONS

This application is a continuation-in-part of parent International Application No. PCT/IN2011/000612, published as WO 2012/032544, filed on Sep. 7, 2011, which claims priority to Indian Application No. 2296/CHE/2010, filed on Sep. 11, 2010. This application is also a continuation-in-part of U.S. patent application Ser. No. 13/146,965, published as U.S. Patent Publication 2011/0280951, which is a national stage application based on International Application No. PCT/IN2010/000053, filed on Feb. 2, 2009, which claims priority to Indian Application No. 224/CHE/2009, filed on Feb. 2, 2009. The entire disclosures of the prior applications are hereby incorporated by reference.

FIELD OF INVENTION

The invention discloses a herbal ingredient selected from extracts and fractions standardized to at least one frullanolide/eudesmanoid sesquiterpene compound(s) derived from *Sphaeranthus indicus* or their composition(s) as natural energy enhancer to provide an onset and steady maintenance of energy and mental alertness in a mammal.

The invention further relates to food ingredient formulations such as beverages, dietary ingredient formulation, snacks and energy drinks containing the above said herbal ingredient or its composition(s) for onset and steady maintenance of energy and mental alertness such as enhancing physical activity, physical fitness, mental alertness, energy levels, stamina levels, circulatory health, blood vessel health or for better physical and mental health.

BACK GROUND OF THE INVENTION

Physical activity, such as exercise, particularly in the heat, places a demand on the body's carbohydrate stores, such as muscle glycogen, liver glycogen, and plasma glucose. Loss of water, redistribution and loss of electrolytes, and the depletion of endogenous carbohydrate reserves are primary causes of fatigue/tiredness that impairs one's work capacity. To maintain the body's physical capabilities, it is essential that water, electrolytes, carbohydrate, and other nutrients be provided in a timely and appropriate manner. Fluid replacement during physical activity has been shown to be effective in preventing dehydration and hyperthermia.

The basic force and condition behind all activities of human life is the presence of energy. Energy is the vital principle needed to sustain life and it is required for every aspect of existence—every act uses energy—thinking, feeling, walking, eating, drinking, dreaming, breathing etc. Energy is felt and experienced upon its expenditure. The energy we experience immediately after eating (such as sweets), or the hype we get following the consumption of coffee is from the expenditure of energy from body's energy reserves, not through its accumulation. Age, fatigue and stress make people feel deficient in energy. This drag in energy very often compromises body's mental alertness. Addressing body's energy demands properly, will increase one's efficiency at work place and in personal management.

Dietary supplements are used by physically active people or weak people to increase their physical performance, physical fitness, improve their health, or reduce the potentially negative consequences of physical activity such as injury and chronic fatigue, or suppressed immune function.

Many energy beverages, supplements and food ingredient formulations are presently available in the market. However, these are fully loaded with disaccharides, carbohydrate complexes, proteins, amino acids and vitamins along with numerous other agents. Many of these formulations act too quickly to give rise instant energy and not maintained over sustained period of time. Besides, these formulations tend to increase the blood glucose levels sharply and this is followed by their rapid depletion. This might some times lead to complications. Natural supplements, which improve the feeling of being energetic, general agility, endurance and mental alertness are thus in great demand. Studies are in process in many research groups across the globe to develop a superior product to address the above requirements.

Therefore, the present invention addresses the existing need in the art by providing an ingredient(s) or composition(s) that provides energy and/or mental alertness. Thus, the present invention provides ingredient(s) and/or composition(s) capable of increasing energy levels for an extended period of time in a mammal to enhance both energy levels and mental alertness and thus solves these needs.

SUMMARY OF INVENTION

In a major embodiment, the invention discloses a herbal ingredient selected from extracts and fractions standardized to at least one frullanolide/eudesmanoid sesquiterpene compound(s) derived from *Sphaeranthus indicus* or their composition(s) for onset and steady maintenance of energy and mental alertness. The *sphaeranthus* derived ingredient and its compositions are useful for enhancing physical activity, physical fitness, mental alertness, energy levels, stamina levels, circulatory health, blood vessel health or for better physical and mental health in a mammal.

In another embodiment, the invention relates to the preparation of dietary supplements, food ingredient formulations such as beverages, snacks and energy drinks containing the above said ingredient(s) or its composition(s) for onset and steady maintenance of energy and mental alertness. The formulation is useful for enhancing physical activity, physical fitness, mental alertness, energy levels, stamina levels, circulatory health, blood vessel health or for better physical and mental health in a mammal.

In a further embodiment, the extracts or fractions are standardized to 7-hydroxyfrullanolide, its analogs or their compositions for onset and steady maintenance of energy; mental alertness and for enhancing physical activity, physical fitness, mental alertness, energy levels, stamina levels, circulatory health, blood vessel health or for better mental health in warm blooded animals in need thereof.

In yet another embodiment, the invention provides compositions described above comprise at least one herbal ingredient selected from extract or fraction standardized to at least one frullanolide/eudesmanoid sesquiterpene compound(s) derived from *Sphaeranthus indicus* in combination with at least one ingredient selected from extract(s), fraction(s), active compound(s), phytochemical(s), derived from plant(s), animal(s) or microorganisms with proven therapeutic health benefits; pharmaceutically or dietetically acceptable agents, active ingredients, vitamins, amino acids and minerals.

In still another embodiment, one or more herbal ingredients derived from *Sphaeranthus indicus* or their compositions are useful for onset and steady maintenance of energy;

mental alertness and for enhancing physical activity, physical fitness, mental alertness, energy levels, stamina levels, circulatory health, blood vessel health or for better mental health in warm blooded animals in need thereof.

In another embodiment, the invention provides a method of increasing natural energy to provide an onset and steady maintenance of energy and mental alertness in a mammal, wherein the method comprises supplementing or treating the said mammal with at least one herbal ingredient selected from the extracts, fractions, compounds; extracts or fractions standardized to active compounds derived from *Sphaeranthus indicus* or their compositions.

DETAILED DESCRIPTION OF INVENTION

For the purpose of this invention, the phrase 'herbal ingredient' OR 'herbal ingredients' OR 'said herbal ingredients' used in the specification and claims of the present invention refer to the extract(s), fraction(s); extract(s) or fraction(s) standardized to at least one frullanolide/eudesmanoid sesquiterpene compound(s) derived from *Sphaeranthus indicus* or their composition(s). The phrase 'herbal ingredient' OR 'herbal ingredients' is used interchangeably through out the specification and the same may be appreciated as such by the person skilled in the art.

The word 'composition' OR 'compositions' OR 'mixture' OR 'mixtures' determine the combination of one or more ingredients selected from extract(s), fraction(s) or compound(s) derived from *Sphaeranthus indicus* or other biologically active ingredients.

The phrase 'biologically active ingredient' or 'biologically active ingredients' refers to other component(s) used for making compositions and selected from extract(s), fraction(s), active compound(s), phytochemical(s); powder(s) derived from plant(s), animal(s) or microorganisms with proven therapeutic health benefits; pharmaceutically or dietetically acceptable active ingredients, vitamins, amino acids or minerals.

The phrase 'weak people' means those individuals who may or may not be suffering from a disease and the weakness can be of physical or mental.

The word 'subject' OR 'subjects' means warm blooded animals, cold blooded animals, birds, horses, human beings or mammals of any sex.

The inventors during their search for new anti-obese supplements have screened a large number of plant extracts for anti-adipogenesis activity using an in vitro assay in 3T3-L1 pre-adipocyte cells and found that extracts of *Sphaeranthus indicus* showed potent anti-adipogenic activity. Subsequent studies have shown that *Sphaeranthus indicus* can potently ameliorate a wide range of metabolic protein markers directly related to obesity, diabetes, cardiovascular diseases and other metabolic disorders. The anti-obese efficacy of *Sphaeranthus indicus* was confirmed in an in vivo study in diet induced obesity and diet induced metabolic syndrome models of Sprague Dawley rats. The details of above experiments and the study results are described in inventor's previous Indian patent application and the corresponding PCT application 224/CHE/2009 filed $2^{nd}$ Feb., 2009; PCT/IN2010/000053 filed $1^{st}$ Feb., 2010.

In various embodiments, studies were conducted using *Sphaeranthus indicus* extract standardized to 5% 7-hydroxyfrullanolide (LI12508) and a composition (LI12507F) containing *Sphaeranthus indicus* extract standardized to 5% 7-hydroxyfrullanolide in combination with *Garcinia mangostana* extract standardized to 10% α-mangostin (LI80018) to assess their efficacy as an anti-obese supplement in a double blind placebo controlled study in obese human subjects. Sixty obese subjects (27.6% male; 72.4% female; ages 22-50 years) were included in a randomized, double-blind, placebo-controlled study of 56 days duration. The participants (BMI 30 to 40) were randomized into three groups; placebo, LI12508 group and LI12507F group. The participants received either 600 mg/day of LI12508 and 800 mg of LI12507F formulation in two divided doses or two identical placebo capsules and all of them remained on a calorie-controlled diet (2000 Calories/day) and 30 min walking for 8 weeks. Various parameters including, physical, anthropomorphic, biochemical and questionnaire based evaluation including quality of life. The *S. indicus* extract (LI12508) and its formulation LI12507F provided significant reduction in body weight in both the treatment groups and also indicated promise for their potential use in controlling serum triglyceride levels. In addition, both LI12508 and LI12507F also showed unexpectedly improved quality of life and improved energy, exercise ability and endurance in subjects supplemented with the treatments when compared the placebo treated group. This includes increased mobility, increased walking speed, increased walking distance, lack of fatigue, feeling untired, feeling light and active.

Even though a few selected extracts have been used in this study, this invention covers all extracts, active fractions and active compounds of the *Sphaeranthus indicus*, which comprises the active ingredient 7-hydroxyfrullanolide or other active ingredient(s) in the range of 0.1% to 99.9%. Preferably any organic solvent extract of *Sphaeranthus indicus* or a fraction or pure compound derived from the extract with or without standardization to 7-hydroxyfrullanolide can be used. The medium for obtaining active extract may be selected from either organic solvents or water or mixtures of organic solvent and water, preferably an organic solvent. The list of organic solvents include but not limited to hexane, dichloromethane, chloroform, ethyl acetate, acetone, methanol, ethanol, n-butanol, iso-propanol, methyl isobutyl ketone etc or the mixtures thereof. The crude extracts may be used as they are as a medicament or for making the compositions. Alternatively, the extracts may be enriched to any designated concentration of 7-hydroxyfrullanolide or one or more active ingredients in the range of 0.1% to 99.9% using solvent partitions or washings or column chromatography on silica or reversed phase silica or resin column using organic or aqueous solvents or mixtures thereof or crystallizations or combinations thereof prior to using them directly for desired health application of the invention or for making the compositions.

In various embodiments, a *Sphaeranthus* indicus derived component is selected from the extracts, fractions, active compounds and phytochemicals, or mixtures thereof, wherein the concentration of active compound 7-hydroxyfrullanolide/other frullanolide/eudesmanoid sesquiterpene(s)/other phytochemicals in the extract(s) and fraction(s) derived from *Sphaeranthus indicus* is between 0.001% to 100%, preferably 0.01 to 99%, more preferably 0.01 to 95% by weight. In various embodiments, the *Sphaeranthus indicus* derived component has a concentration of the active compound 7-hydroxyfrullanolide of between 5% and 21%.

Encouraged by this surprising result, the inventors evaluated the ability of the study products LI12508 and LI12507F to enhance the ATP levels in a cellular model. The intracellular ATP level in the cells treated with LI12508 and LI12507F were measured by luminescence based ATP detection assay system, ATPlite (PerkinElmer Inc., Waltham, Mass.). Briefly, equal number of L6 Rat myocytes was plated in each well of a 96-well cell culture plate and cultured in DMEM supplemented with 10% FBS. The cells were treated with test samples (LI12508 and LI12507F) at 50 pg/mL. Intracellular ATP level was quantitatively estimated from a standard curve plotted with luminescence units vs. known concentrations of ATP and the results compared with that obtained for the control treated sample as summarized in the table 1. Both the *Sphaeranthus indicus* extract standardized to 5% 7-HF (LI12508) and its composition (LI12507F) significantly increased the ATP levels in the rat myocyte cells, when compared to the control.

The Energy Endurance potential of LI12508 following oral administration was further evaluated in male and female Swiss albino mice. Swiss albino mice of 20 weeks old were selected and examined for health status and divided into three groups each consisting of 6 animals (3 males and 3 females). The control group animals were treated p.o with 0.5% of CMC and treatment groups were treated once a day with the test compound LI12508 at 100 mg/kg or 250 mg/kg body weight for one week. On day 7, one hour after the treatment, the animals were tested for energy endurance with force swimming test using the SMART video tracking system (Panlab S.L.U). Resting time and its percentage, slow moving and its percentage, fast moving and its percentage, total path length of swimming and average velocity were analyzed using SMART video tracking software and the data is summarized in table 2.

Figure 1:
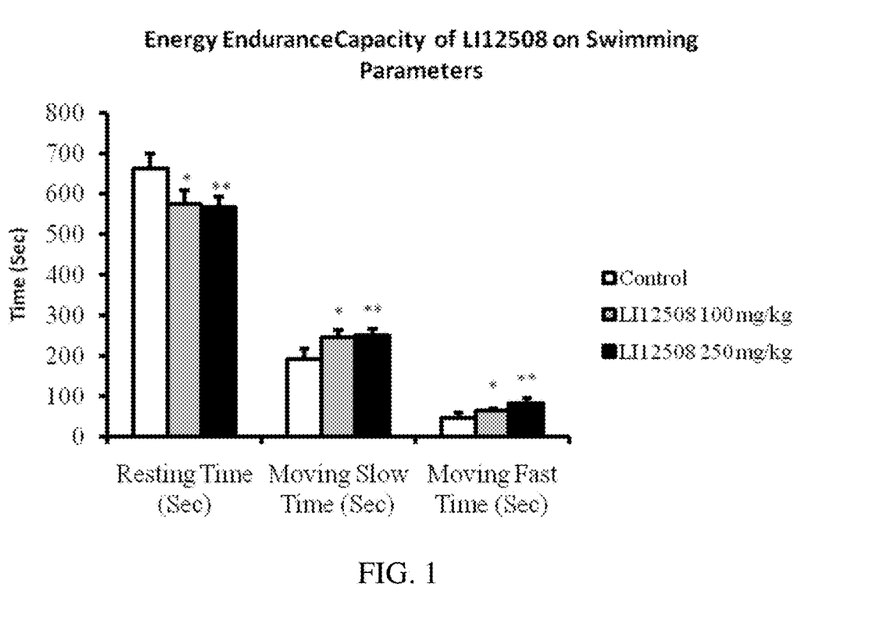
FIG. 1: Figure shows Energy endurance capacity of LI12508 on swimming parameters. The bars represent resting time, moving slow time and moving fast times in seconds. Values are expressed as Mean±S.E.M, n=6. * $p<0.05$ and ** $p<0.01$ as compared to Control (ANOVA followed by Tukey's test)
Figure 2:
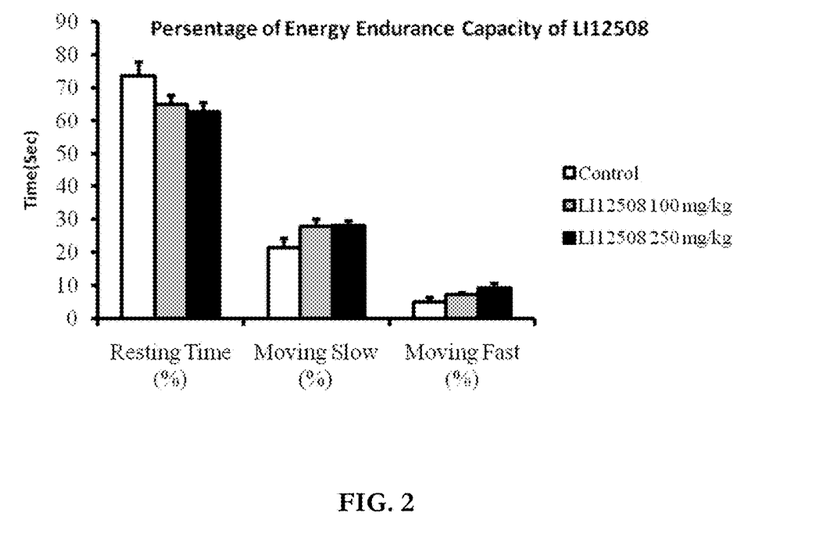
FIG. 2: Figure shows Percentage of energy endurance capacity of LI12508. The bars represent percentage resting time, moving slow time and moving fast times in seconds.
Figure 3:
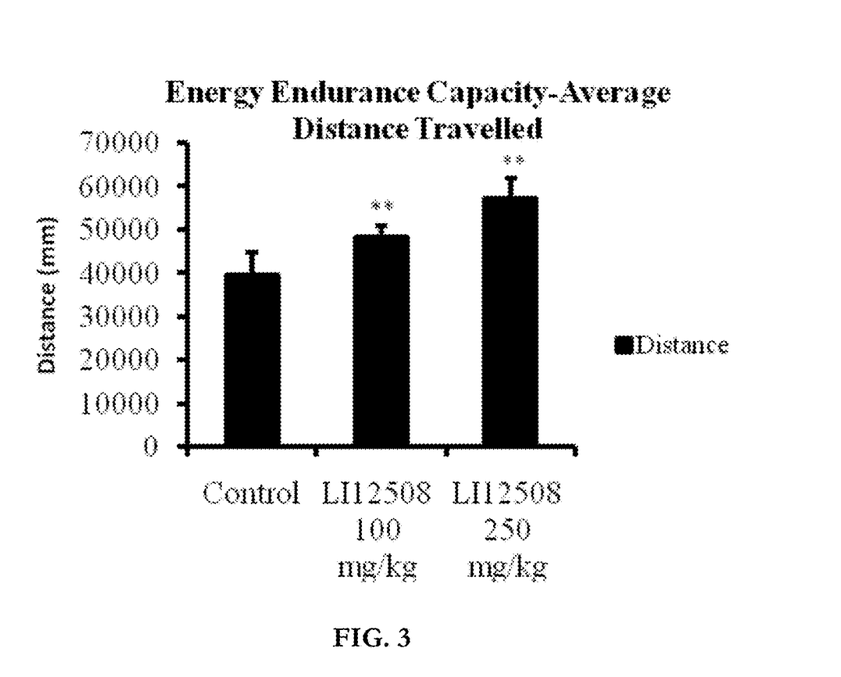
FIG. 3: Figure shows Energy endurance capacity-Average distance travelled in mm. The bars represent average travelled by the control group and treatment group of animals supplemented with 100 mg/kg or 250 mg/kg body weight. Values are expressed as Mean±S.E.M, n=6. ** $p<0.01$ as compared to Control (ANOVA followed by Tukey's test.
Figure 4:
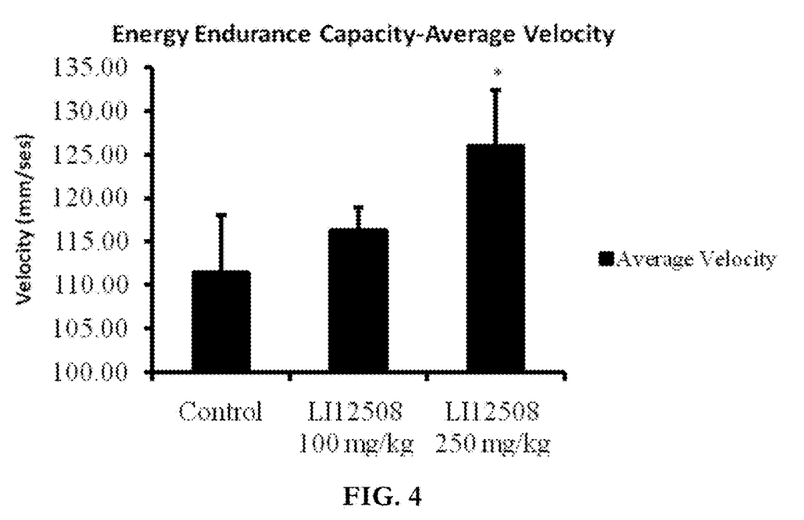
FIG. 4: Figure shows Energy Endurance capacity. The bars represent Average velocity exhibited by the control group and treatment group (100 mg/kg or 250 mg/kg body weight) of animals. Values are expressed as Mean±S.E.M, n=6. * $p<0.05$ as compared to Control (ANOVA followed by Tukey's test).

Based on the results obtained, there was a dose dependent decrease in mean resting time in animals supplemented with 100 or 250 mg/kg of the test substance, LI12508. This mean reduction in resting time observed in treated groups is statistically significant when compared to control. In addition, the mean increase in slow swimming time, fast swimming time and average distance covered in both the treatment groups (100 mg/kg and 250 mg/kg) supplemented with LI12508 is also significant, when compared to control group as shown FIGS. 1 to 3. Significant increase in average velocity was observed in animals treated with 250 mg/kg p.o as compared to control group as depicted in FIG. 4. The increase in mean slow swimming time and mean fast swimming time reveals that the animals treated with LI12508 (100 mg/kg and 250 mg/kg) preferred to swim for a longer period of time instead of resting as observed in vehicle treated control animals. The increase in mean swimming velocity observed in 250 mg/kg LI12508 treated animals, further support the increase in mean distance covered by the animals in the shorter period of time as compared to other two groups. This indicates the animals treated with LI12508 were very active and energetic during 15 minutes forced swimming period and could tend to swim either slow or fast most of the time rather than resting when compared to control group treated with 0.5% CMC. The longer distance covered at higher velocity and shorter resting times observed in LI12508 treated animals indicate that LI12508 improves energy and endurance. Hence, it is obvious that supplementation of *Sphaeranthus indicus* extract can increase the energy levels and endurance potential.

The forgoing demonstrates that *Sphaeranthus indicus* extract standardized to 5% 7-hydroxyfrullanolide (LI12508) and its composition in combination with *Garcinia mangostana* extract standardized to 10% α-mangostin (LI12507F) could be potent natural supplements to provide an onset, steady maintenance of energy, physical endurance and mental alertness in humans and animals.

Accordingly, in a major embodiment, the invention discloses a herbal ingredient selected from extracts and fractions standardized to at least one frullanolide/eudesmanoid sesquiterpene compound(s) derived from *Sphaeranthus indicus* or their composition(s) for onset and steady maintenance of energy and mental alertness. The *sphaeranthus* derived ingredients and its compositions are useful for enhancing physical activity, physical fitness, mental alertness, energy levels, stamina levels, circulatory health, blood vessel health or for better physical and mental health in a mammal.

In another embodiment the invention discloses the composition consisting of *Sphaeranthus indicus* derived herbal ingredient in combination with at least one biologically active ingredient selected from extract of *Garcinia mangostana* fruit rind, *Osmium basilicum*, *Zingiber officinalis*, *Tribulus terrestris*, vitamins, amino acids, taurine, an extract of *Ginkgo biloba*, *Rhodiola* and an extract of guarana, optionally in combination with an excipient, diluent or carrier as a natural energy enhancer to provide an onset and steady maintenance of energy and mental alertness in a warm blooded animal or mammal in need thereof.

In another embodiment, the invention relates to at least one *Sphaeranthus indicus* derived herbal ingredient selected from the extracts and fractions standardized to 7-hydroxyfrullanolide or its analogs or mixtures thereof as a natural energy enhancer to provide an enhanced physical or mental performance, onset and steady maintenance of energy and mental alertness in a mammal.

In yet another embodiment, the invention relates to a composition comprising at least one herbal ingredient selected from extract or fraction standardized to at least one frullanolide/eudesmanoid sesquiterpene compound(s) derived from *Sphaeranthus indicus* or their composition(s) in combination with at least one ingredient selected from the extracts, fractions or compounds derived from *Garcinia mangostana*, further optionally containing at least one ingredient selected from excipient, diluent, vitamins or amino acids, as a natural energy enhancer for enhancing physical or mental performance, onset and steady maintenance of energy enhancing physical activity, physical fitness, mental alertness, energy levels, stamina levels, circulatory health, blood vessel health or for better mental health in a mammal.

In yet another embodiment, the invention provides a composition comprising at least one herbal ingredient selected from the extracts, fractions or compounds derived from *Sphaeranthus indicus* in combination with at least one ingredient selected from the extracts, fractions or compounds derived from *Garcinia mangostana*, optionally containing at least ingredient selected from excipient, diluent, vitamins or amino acids, as a natural energy enhancer for enhancing physical or mental performance, onset and steady maintenance of energy and mental alertness in a mammal.

In another embodiment of the invention provides a composition comprising at least one herbal ingredient selected from the extracts or fractions standardized to at least one frullanolide/eudesmanoid sesquiterpene compound such as 7-hydroxyfrullanolide (1) derived from *Sphaeranthus indicus* in combination with a *Garcinia mangostana* extract standardized to α-mangostin (2) or γmangostin (3) and further optionally in combination with suitable excipients as a natural energy enhancer to provide an enhancing physical or mental performance, onset and steady maintenance of energy, mental alertness, for enhancing physical activity, physical fitness, energy levels, stamina levels, circulatory health, blood vessel health or for better mental health in a mammal.

Structures of 7-Hydroxyfrullanolide (1),
α-mangostin (2) & γ-mangostin (3)

2. R = CH₃
3. R = H

In still yet another embodiment of the invention provides a composition comprising at least one herbal ingredient selected from the extracts or fractions standardized to 5% 7-hydroxyfrullanolide derived from *Sphaeranthus indicus* in combination with a *Garcinia mangostana* extract standardized to 10% α-mangostin and suitable excipients as a natural energy enhancer to provide an enhancing physical or mental performance, onset and steady maintenance of energy and mental alertness in a mammal.

In another important embodiment, examples of improved physical performance include increased stamina and improved speed, strength, power, endurance, flexibility, agility, balance, focus coordination, reaction time, fatigue recovery and also increase of sex stamina. Examples of improved mental performance include improved sharpness, attention span, mental alertness, cognitive functions, mood elevation, and recovery or reduction of mental fatigue (e.g., following a high-intensity physical exercise).

In another embodiment, the invention includes the preparation of dietary supplements, food ingredient formulations such as beverages, snacks and energy drinks containing the above said ingredient(s) or its composition(s) for enhancing physical activity, physical fitness, mental alertness, energy levels, stamina levels, circulatory health, blood vessel health or for better mental health in warm blooded animals in need thereof.

In yet another embodiment the invention provides at least one herbal ingredient selected from the extract(s), fraction(s), compound(s), extracts or fractions standardized to active compound(s)/7-hydroxyfrullanolide or its analogs derived from *Sphaeranthus indicus* and compositions as natural enhancers of energy instantly, physical performance in warm blooded animals in need thereof.

In another embodiment the extracts and/or fractions standardized to 7-hydroxyfrullanolide, its analogs or their compositions can be used for enhancing physical performance or energy levels in warm blooded animals.

In yet another embodiment the invention provides compositions comprising biologically active ingredients in combination with one or more components selected from extract(s), fraction(s), active compound(s), phytochemical (s); powder(s) derived from plant(s), animal(s) or microorganisms with proven therapeutic health benefits; pharmaceutically or dietetically acceptable agents, active ingredients, vitamins, amino acids or minerals.

In the other embodiment, the invention discloses composition containing *Sphaeranthus indicus* extract or fraction standardized to 7-hydroxyfrullanolide or its analogs in combination with at least one biologically active ingredient selected from an extract of *Garcinia mangostana, Osmium basilicum, Zingiber officinalis, Tribulus terrestris*, vitamin B, vitamin C, Vitamin E, taurine, an extract of *ginkgo biloba, Rhodiola* and an extract of guarana.

In another embodiment of the invention discloses the composition consisting of *Sphaeranthus indicus* derived herbal ingredient in combination with at least one biologically active ingredient selected from extract of *Garcinia mangostana* fruit rind, *Osmium basilicum, Zingiber officinalis, Tribulus terrestris*, vitamins, amino acids, taurine, an extract of *Ginkgo biloba, Rhodiola* and an extract of guarana, optionally in combination with an excipient, diluent or carrier as a natural energy enhancer to provide an onset and steady maintenance of energy and mental alertness in a warm blooded animal or mammal in need thereof.

In another embodiment the invention discloses the compositions wherein the extract of *Garcinia mangostana* fruit rind is standardized to α-mangostin or γ-mangostin or both and optionally in combination with at least one excipient/diluent as a natural energy enhancer to provide an onset and steady maintenance of energy and mental alertness in a warm blooded animal or mammal in need thereof.

In a further exemplary embodiment, the biologically active ingredients of the present invention for preparing the composition may further include one or more of the non-limiting components such as vitamins selected from B vitamins, including thiamine, riboflavin, niacin, pantothenic acid, pyridoxine, biotin, cyanocobalamin, choline and/or folic acid, including the reduced forms of folic acid such as but not limited to folinic acid, calcium folinate and methyltetrahydrofolate. The B-complex vitamins are also water soluble vitamins that aid the breakdown of carbohydrates into glucose to provide energy for the body, the breakdown of fats and proteins to aid the normal functioning of the nervous system, and muscle tone in the stomach and intestinal tract. Particular forms of B vitamins in the composition may include d-Calcium pantothenate, niacinamide, pyridoxine hydrochloride, and thiamine mononitrate; or amino acids.

In another embodiment the *Sphaeranthus indicus* derived herbal ingredient selected from the extracts or fractions standardized to 7-hydroxyfrullanolide or its analogs or mixtures thereof and/or their composition(s) increases circulation, metabolism efficiency, regulates neurotransmitters and boosts oxygen levels in the brain. Benefits of enhanced circulation in the brain include improved short and long term memory, increased reaction time and improved mental clarity.

In yet another embodiment the said herbal ingredients or their composition(s) are useful for enhancing energy levels, mental alertness, stamina levels, circulatory health and blood vessel health as well as for providing nutritional support. It can also be used as an energy booster for patients in need thereof, e.g., cancer patients or AIDS patients. Moreover, it is useful for enhancing athletic performance in both humans and animals, e.g., horses.

In another embodiment the said herbal ingredients and/or their composition(s) can be taken e.g. by performance athletes, those engaged in endurance and multi-discipline sports, aged and sick persons in order to increase mental and physical efficiency and to repress susceptibility to illnesses, such as cold, bacterial and viral infections, in a natural manner. The present ingredients and compositions may be formulated as a "fitness drink" that can be taken with breakfast or in the form of a concentrate from which such a drink can be regularly used.

In another embodiment 7-hydroxyfrullanolide or its analogs obtained naturally, synthesized or semi-synthesized can be useful for enhancing physical or mental performance.

In another embodiment one or more of the analogs of 7-hydroxyfrullanolide that can be used for preparing compositions comprise of frullanolides; 11α,13-dihydro-3α,7α-dihydroxy-4,5-epoxy-6β,7-eudesmanolide; 11α,13-dihydro-7α-acetoxy-3β-hydroxy-6β,7-eudesm-4-enolide; 3-keto-β-eudesmol; 11α,13-dihydro-3α,7α-dihydroxyeudesm-4-en-6α,12-olide; 11α,13-dihydro-3α,7α-dihydroxyfrullanolide; 11α,13-dihydro-7α,13-dihydroxyfrullanolide; 11α,13-dihydro-7α-hydroxy-13-methaoxyfrullanolide; 2α,7α-dihydroxy-4-en-11,13-dihydroeudesm-6,12-olide; 2α-hydroxycostic acid; 3-keto-7α-hydroxyeudesm-4-en-6,12-olide (cryptomeridiol); 4-epicryptomeridiol; sphaeranthanolide; 2α-hydroxysphaerantholide; 2α-acetoxysphaerantholide; 2α,7α-dihydroxysphaerantholide; 2α-acetoxy-7α-hydroxysphaerantholide and 2α-acetoxy-5α-hydroxyisosphaerantholide.

The concentration of *Sphaeranthus indicus* derived 7-hydroxyfrullanolide or frullanolide/eudesmanoid sesquiterpene compounds in the present invention individually or together varies in the range of 0.01% to 99.99%.

The composition wherein, the concentration of *Garcinia mangostana* fruit rind extract, α-mangostin and γ-mangostin individually or jointly varies from 0.01% to 99.99%.

In another embodiment the herbal ingredient(s) or composition(s) of the present invention are useful to improve aerobic performance and capacity by influencing lactic acid metabolism and reducing fatigue as well as for alleviation of one or more of the biological energy markers including but not limited to ATP levels/production; Nitric Oxide levels, NADH balance, leptin levels, adipocytes derived peptide In another embodiment the herbal ingredient(s) can further be combined with one or more biological active ingredients comprising anti-diabetic, anti-hyperlipidemic, anti-obesity, anti-hypertensive, anti-platelet aggregation, anti-infective, anti-atherosclerotic, anti-inflammatory, anti-oxidant and bio-enhancing activity.

In a further exemplary embodiment, the composition may contain an effervescent. As is understood, an effervescent is an agent comprising one or more compounds which, act individually or together, evolve a gas on contact with water. The gas evolved is generally oxygen or, most commonly, carbon dioxide. Preferred effervescent agents comprise an acid component and a base component that react in the presence of water to generate carbon dioxide gas. The acid component can comprise one or more acids and the base component can comprise one or more bases. Preferably, the base component comprises an alkali metal or alkaline earth metal carbonate or bicarbonate and the acid component comprises an aliphatic carboxylic acid. Non-limiting examples of suitable bases for use in a base component include carbonate salts (e.g., calcium carbonate), bicarbonate salts (e.g., sodium bicarbonate), sesquicarbonate salts, and mixtures thereof. Sodium bicarbonate is a preferred base.

Non-limiting examples of suitable acids for use in an acid component include citric acid, lactic acid, glutaric acid, phosphoric acid, acetic acid, tartaric acid, malic acid, fumaric acid, adipic acid, succinic acid, oxaloacetate, acid anhydrides of such acids, acid salts of such acids, and mixtures thereof. Citric acid is a preferred acid.

In a further exemplary embodiment, the composition may contain sweeteners. Preferred sweeteners for use in the present invention are sugars and sugar alcohols such as sucrose, fructose, dextrose, maltose, lactose, high fructose corn syrup solids, invert sugar, sugar alcohols, including sorbitol, as well as mixtures of these sugars and sugar alcohols. In order to deliver lower levels of solids per dosage, it may be preferred to use a higher intensity sweetener with the sugar or sugar alcohol. These higher intensity sweeteners include saccharin, cyclamates, acesulfame K, L-aspartyl-L-phenylalanine lower alkyl ester sweeteners (e.g., aspartame); L-aspartyl-D-alanine amides; L-aspartyl-D-serine amides; L-aspartyl-L-1-hydroxymethylalkaneamide sweeteners; L-aspartyl-1-hydroxyethylalkaneamide sweeteners; and L-aspartyl-D-phenylglycine ester and amide sweeteners. Further sweeteners contemplated for use with the compositions disclosed herein include sweeteners derived from stevia, sweeteners derived from *momordica grosvenorii*, and sweeteners derived from mogrosides. A particularly preferred sweetener system is a combination of sucralose with acesulfame K and corn syrup solids.

In another exemplary embodiment, the composition may be dissolved in water or in other liquids suitable for human consumption.

In another embodiment of the invention the various suitable solvents that can be used for preparing the extracts and fractions or extracting or fractionating the herbs such as *Sphaeranthus indicus, Garcinia mangostana* include but not limited to C1-C5 alcohols, like ethanol, methanol; water and mixtures thereof; C1-C7 hydrocarbons such as hexane; esters like ethyl acetate and the like and mixtures thereof.

In another embodiment, the ingredients and compositions of the present invention may be formulated in dry form, liquid form, food product, dietary supplement or any suitable form such as tablet, a capsule or a soft chew.

In another embodiment the herbal ingredient(s) or composition(s) can be delivered in the form of controlled release tablets, using controlled release polymer-based coatings by the techniques including nanotechnology, microencapsulation, colloidal carrier systems and other drug delivery systems.

In another embodiment of the invention provides herbal ingredient(s) or their compositions nutritional/dietary supplements can be contemplated/made in the dosage form of healthy foods, or food for specified health uses such as solid food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

The flavorant(s) that may be included in the composition are not relevant to the inventive concepts disclosed herein, and those skilled in the art are familiar with the wide range of flavorants available. Therefore, any suitable flavorant or combination of flavorants, natural and/or artificial, is within the contemplated scope of the present disclosure.

In another exemplary embodiment, the composition may further include food colorants to improve the visual appearance of a drink prepared with the composition.

The flavoring agent or agents may provide a fruit flavor, cola flavor, vanilla flavor, or a chocolate flavor, by way of example and not by way of limitation. Sweeteners, natural or synthetic, such as sucrose, sucralose, aspartame, and/or acesulfame potassium, neotame, polydextrose, glycerin, sorbitol, and xylitol, may be used, by way of example and not by way of limitation. Coloring agents may be added. Agents such as citric acid, fumaric acid, adipic acid, tartaric acid, and in some instances lactic acid may be added to adjust for tartness.

Additional ingredients in the form of analgesics (e.g. aspirin), mild stimulants other than caffeine, which is mentioned above (e.g. green tea), or relaxants (e.g. melatonin), may be added in specialized product applications.

In other embodiment, the herbal ingredients and composition of this invention are useful in treating mitochondrial deficiencies in both humans and animals. It also can be used for enhancing or maintaining physical or mental performance, reducing infection in physically stressed athletes or non-athletes from intense physical exercises. Moreover, it can be an activator of Sirtuin.

In another exemplary embodiment the biologically acceptable ingredients or compositions can further be combined with one or more pharmaceutically or dietetically acceptable excipients, carriers and diluents, comprising glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol, propylene glycol and polyethylene glycol, various animal and vegetable oils, white soft paraffin, paraffin and wax.

In still another embodiment, the invention features a method for enhancing physical or mental performance, steady maintenance of energy, physical endurance and mental alertness in humans and animals, wherein the method comprises administering to a subject in need thereof an effective amount of at least one herbal ingredient selected from the extract(s), fraction(s), compound(s), extracts or fractions standardized to active compound(s)/7-hydroxyfrullanolide derived from *Sphaeranthus indicus* and compositions thereof. Examples of improved physical performance include increased stamina and improved speed, strength, power, endurance, flexibility, agility, balance, focus coordination, reaction time, fatigue recovery and also increase of sex stamina. Examples of improved mental performance include improved sharpness, attention span, mental alertness, cognitive functions, mood elevation, and recovery or reduction of mental fatigue (e.g., following a high-intensity physical exercise). By properly administrating the ingredient or composition, a subject's physical or mental performance can be greatly enhanced without deleterious side effects.

In still another embodiment, the invention features use of at least one herbal ingredient selected from the extract(s), fraction(s), compound(s), extracts or fractions standardized to active compound(s)/7-hydroxyfrullanolide derived from *Sphaeranthus indicus* and compositions thereof to enhance physical activity, physical fitness, mental alertness, enhancing energy levels, stamina levels, circulatory health, blood vessel health and for better mental health in warm blooded animal or humans or animals.

In still another embodiment of the invention, use of at least one herbal ingredient selected from the extract(s), fraction(s), compound(s), extracts and fractions standardized to active compound(s)/7-hydroxyfrullanolide derived from *Sphaeranthus indicus* and compositions thereof for the preparation of a medicament useful for enhancing physical or mental performance, steady maintenance of energy, physical endurance and mental alertness in humans and animals.

Those of ordinary skill in the art will appreciate that changes could be made to the embodiments described above without departing from the broad inventive concept thereof. It is understood, therefore, that this invention is not limited to the particular embodiments or examples disclosed, but is intended to cover modifications within the objectives and scope of the present invention as defined in the specification.

Example 1

*Sphaeranthus indicus* Methanol Extract (LI12500):

*Sphaeranthus indicus* flower heads (1 kg) were taken in a round bottom flask and extracted with methanol (8 L) at 60-65° C. temperature for 2 h. The extract was filtered and the spent raw material was re-extracted twice with methanol (2×6 L) under similar conditions. The combined extract was fine filtered and concentrated over a climbing film evaporator to obtain a residue (110 g). The methanol extract (LI12500) showed 11% of 7-hydroxyfrullanolide by HPLC method of analysis.

*Sphaeranthus indicus* Methanol Extract Standardized to 5% 7-hydroxyfrullanolide

*Sphaeranthus indicus* methanol extract containing 7-hydroxyfrullanolide as obtained above was diluted with microcrystalline cellulose and magnesium stearate along with 2% by weight of aerosil to obtain *Sphaeranthus indicus* powdered methanol extract standardized to 5% 7-hydroxyfrullanolide (LI12508).

Example 2

*Sphaeranthus indicus* Ethanol Extract:

*Sphaeranthus indicus* flower heads (1 kg) were taken in a RB flask and extracted with ethanol (8 L) at 60-65° C. temperature for 2 h. The extract was filtered and the spent raw material was re-extracted twice with ethanol (2×6 L) under similar conditions. The combined extract was fine filtered and concentrated over a climbing film evaporator to obtain a residue (98 g). The ethanol extract showed 12% of 7-hydroxyfrullanolide by HPLC method of analysis.

Example 3

Garcinia mangostana Rind Methanol Extract (LI80013):
Shade dried fruit rind (1 Kg) of Garcinia mangostana was pulverized to coarse powder, and extracted with 90% methanol (5 L) for 2 hrs at 60-65'C. The solvent was separated from the raw material by filtration. Extraction process was repeated three times using 90% methanol (2×3 L & 1×2 L). The combined extracts were fine filtered and concentrated under reduced pressure and allowed to precipitate at ambient temperature. The solid separated was filtered to give a dry powder (150 g, α-mangostin: 21% and γ-mangostin: 2.5%).

Example 4

Garcinia mangostana Methanol Extract Standardized to 10% α-Mangostin:
Garcinia mangostana methanol extract containing α-mangostin as obtained above (example 3) was diluted with microcrystalline cellulose and magnesium stearate along with 2% aerosil to obtain Garcinia mangostana methanol extract standardized to 10% α-mangostin (LI80018).

Example 5

Garcinia mangostana Rind Ethanol Extract:
Shade dried fruit rind (1 Kg) of Garcinia mangostana was pulverized to coarse powder, and extracted with 90% ethanol (5 L) for 2 hrs at 60-65° C. The solvent was separated from the raw material by filtration. Extraction process was repeated thrice using 90% ethanol (2×3 L & 1×2 L). The combined extracts were fine filtered and concentrated under reduced pressure and allowed to precipitate at ambient temperature. The solid separated was filtered to give ethanol extract as a dry powder (136 g, α-Mangostin: 22%).

Example 6

Composition LI12506F: The composition LI12506F was prepared by combining the methanol extract of Sphaeranthus indicus (LI12500) and 90% methanol extract of Garcinia mangostana (LI80013), both as prepared above, in the ratio of 3:1.

Example 7

Formulation LI12507F (Merastin®): The Sphaeranthus indicus powder extract standardized to minimum 5% 7-hydroxyfrullanolide (LI12508) and Garcinia mangostana methanol extract standardized to 10% α-mangostin (LI80018) as prepared above were combined at 3:1 ratio and properly blended to obtain LI12507F.

Example 8

Composition LI12517F:
Composition LI12517F was prepared by mixing unit doses of the following components:
One part of Sphaeranthus indicus ethanol extract (1 g) and
Three parts of Garcinia mangostana 90% ethanol extract (3 g).

Example 9

A study was conducted using Sphaeranthus indicus extract standardized to 5% 7-hydroxyfrullanolide (LI12508) and a composition containing Sphaeranthus indicus extract standardized to 5% 7-hydroxyfrullanolide in combination with Garcinia mangostana extract standardized to 10% α-mangostin (LI12507F) to assess their efficacy as an anti-obese supplement in a double blind placebo controlled study in obese human subjects. Sixty obese subjects (27.6% male; 72.4% female; ages 22-50 years) were included in a randomized, double-blind, placebo-controlled study of 56 days duration. The participants (BMI 30 to 40) were randomized into three groups; placebo, LI12508 group and LI12507F group. The participants received either 600 mg/day of LI12508 and 800 mg of LI12507F formulation in two divided doses or two identical placebo capsules and all of them remained on a calorie-controlled diet (2000 Calories/day) and 30 min walking for 8 weeks. Various parameters including, physical, anthropomorphic, biochemical and questionnaire based evaluation including quality of life have been studied. The S. indicus extract (LI12508) and its formulation LI12507F provided significant reduction in body weight in both the treatment groups and also indicated promise for their potential use in controlling serum triglyceride levels.

Impact of Weight on Quality of Life Questionnaire-Lite Version (IWQOL-Lite) including subjects feedback was administered to all the subjects at each evaluation point including days 0, 14, 28 and 56 was assessed. Subjects expressed improvement in various parameters including increased mobility, increased walking speed, increased walking distance and time, feeling untired, feeling light and active. Number of subjects expressed such improvement in physical ability and endurance was more in supplement groups compared to placebo group.

Both LI12508 and LI12507F also showed unexpectedly improved quality of life and improved energy, exercise ability and endurance in subjects supplemented with the treatments when compared the placebo treated group. This includes increased mobility, increased walking speed, increased walking distance, lack of fatigue, feeling untired, feeling light and active.

Example 10

Intracellular ATP level in the cells treated cells with LI12508 and LI12507F were measured by luminescence based ATP detection assay system, ATPlite (PerkinElmer Inc., Waltham, Mass.). Briefly, equal number of L6 Rat myocytes was plated in each well of a 96-well cell culture plate and cultured in DMEM supplemented with 10% FBS. The cells were treated with different concentrations of test samples (LI12508 and LI12507F) for 4 h and thereafter, to each well 50 ul of cell lysis buffer were added. The vehicle control culture wells received 0.2% DMSO (v/v). Finally, 50 ul of substrate solution was added to each well and incubated at room temperature for 5 min on plate shaker. After 10 minutes of dark adaptation, the luminescence was read in a luminometer (Modulus Multimode Reader, Turner Biosystems Inc., Sunnyvale, Calif.). A serial dilution of an ATP standard solution ranging from $1 \times 10^{-5}$ M to blank was applied to the assay plate. Intracellular ATP level was quantitatively estimated from a standard curve plotted with luminescence units vs. known concentrations of ATP.

TABLE 1

| S. No | Test Product | Code | Dose pg/mL | ATP Concentration |
|---|---|---|---|---|
| 1 | Control | — | — | 2.808 |
| 2 | S. indicus 5% extract | LI12508 | 50 | 3.313 |
| 3 | S. indicus composition | LI12507F | 50 | 6.119 |

Example 11

Evaluation of Energy Endurance Capacity of Herbal Extract in Swiss Albino Mice:

Eighteen Swiss albino mice of 20 weeks old were selected and examined for health status and acclimatized for one week before initiation of the study. The animals were randomly divided into three groups each consisting of 6 animals (3 males and 3 females) corresponding to two doses (100 and 250 mg/kg body weight) of test substance LI12508 and vehicle control. The animals were treated orally with allocated test substances or vehicle daily for 1 week. Swimming exercise (15 min) was initiated after 1 hr of treatment and continued daily for 7 days. Mice were allowed to swim with supporting constant loads (lead fish sinkers, attached to the tail) corresponding to 10% of their body weight, in a acrylic tank filled with water. On day $7^{th}$, this swimming exercise for 15 min was tracked using the SMART video tracking system (Panlab S.L.U). Swimming time or resting time, Distance travelled and velocity of swimming was measured using the tracking software. Resting time and its percentage, moving slow and its percentage, moving fast and its percentage, total path length of swimming and average velocity were analyzed using SMART video tracking software and the data is summarized in table 2. There was a significant decrease in mean resting time and a significant increase in mean slow swimming time, mean fast swimming time and average distance covered in both 100 mg/kg and 250 mg/kg of LI12508 treated group animals when compared to control treated animal group as summarized in the FIGS. 1 to 2. Moreover, animals treated with 250 mg/kg p.o showed a significant increase in average velocity as compared to control group as depicted in FIG. 4.

was fine filtered and concentrated over a climbing film evaporator to obtain residue (174 g). The ethyl acetate extract showed 11% of 7-hydroxy-4,11(13)-eudesmadien-12,6-olide (7-hydroxyfrullanolide) by HPLC method of analysis.

Example 13

*Sphaeranthus indicus* Hexane Extract (LI/DD-II/054A/02):

*Sphaeranthus indicus* flower heads (1.0 kg) were taken in a Soxhlet apparatus and extracted with hexane (6 L) at reflux temperature for 4 h. The extract was fine filtered and the spent raw material was re-extracted twice with hexane (2×4 L). The extracts were combined and concentrated under vacuum to obtain a residue (43 g). The hexane extract showed 21% of 7-hydroxyfrullanolide by HPLC method of analysis.

Example 14

Purification of 7-hydroxyfrullanolide (LI054A01):

The ethyl acetate extract (90 g) of the flower heads of *Sphaeranthus indicus* was subjected to chromatography over a silica column using eluants of increasing polarity from hexane to acetone. The fractions eluted with 20% acetone/hexane were combined and evaporated under vacuum to give a residue (16 g) containing 63% of 7-hydroxyfrullanolide. The residue was subjected to re-chromatography over silica using solvents of increasing polarity from hexane to ethyl acetate. The fractions eluted with 20-25% ethyl acetate/hexane yielded were combined and evaporated and the residue was precipitated from acetonitrile to obtain semi-pure 7-hydroxyfrullanolide (91%). The residue was finally purified on silica column using chloroform/hexane mixtures. The fractions eluted with 25-35% chloroform/hexane were combined and evaporated to give pure 7-hydroxyfrullanolide (7.3 g, 99%).

Example 15

Purification of α-Mangostin and γ-Mangostin:

The methanol extract (90 g) of *G. mangostana* having 32% α-mangostin was subjected to chromatography over a

TABLE 2

Energy Endurance Potential of LI12508 on Forced Swimming Test Parameters

| Parameters Test Article | Distance (cm) | Resting Time (Sec) | Resting Time (%) | Moving Slow Time (Sec) | Moving Slow (%) | Moving Fast Time (Sec) | Moving Fast (%) | Average Velocity |
|---|---|---|---|---|---|---|---|---|
| CMC (Control) | 39588.39 ± 5247.84 | 662.63 ± 36.94 | 73.57 ± 4.10 | 192.74 ± 25.99 | 21.40 ± 2.89 | 45.29 ± 12.96 | 5.03 ± 1.44 | 111.40 ± 6.72 |
| LI12508 100 mg/kg | 48345.11** ± 2549.01 | 574.63* ± 31.56 | 64.83 ± 2.90 | 245.57* ± 19.48 | 27.87 ± 2.33 | 64.09* ± 5.36 | 7.30 ± 0.71 | 116.27 ± 2.71 |
| LI12508 250 mg/kg | 57160.52** ± 4810.60 | 565.71** ± 24.78 | 62.80 ± 2.75 | 252.40** ± 14.82 | 28.02 ± 1.65 | 82.71** ± 12.83 | 9.18 ± 1.42 | 125.96* ± 6.39 |

Values are expressed as Mean ± S.E.M, n = 6.
*p < 0.05,
**p < 0.01 as compared to CMC control (ANOVA followed by Tukey's Test)

Example 12

*Sphaeranthus indicus* Ethyl Acetate Extract (LI/DD-II/054A/01)

*Sphaeranthus indicus* flower heads (2.2 kg) were charged into a pilot extractor and extracted with ethyl acetate (22 L) at reflux temperature for 2 h. The extract was filtered and the spent raw material was re-extracted twice with ethyl acetate (2×13 L) under similar conditions. The combined extract silica column using eluants of increasing polarity from chloroform to methanol. The fractions eluted with 10-15% methanol/chloroform were monitored and the fraction containing α-mangostin were combined and evaporated under vacuum and the residue was crystallized from dichloromethane/methanol mixture to obtain a residue (20 g) containing 99% of α-mangostin. The fractions eluted with 25% methanol/chloroform were monitored and the fraction containing γ-mangostin were combined and evaporated under vacuum and the residue was crystallized from dichloromethane/methanol mixture to residue (2.1 g) containing 99% of γ-mangostin.

Example 16

Process for Preparing Composition 1A, Composition 1B, Composition 1C and Composition 1D:

Composition-1A was prepared by mixing unit doses of the following components: Three parts of *Sphaeranthus indicus* ethyl acetate extract (LI/DD-II/054A/01, 3 g) and one part of *Garcinia mangostana* methanol extract (AR933, 1 g).

Composition 1B was prepared by mixing unit doses of the following components: One part of *Sphaeranthus indicus* ethyl acetate extract (1 g) and three parts of *Garcinia mangostana* methanol extract (3 g).

Composition 1C was prepared by mixing unit doses of the following components: one part of *Sphaeranthus indicus* methanol extract (1 g) and three parts of *Garcinia mangostana* methanol extract (3 g).

Composition 1D was prepared by mixing unit doses of the following components: three parts of *Sphaeranthus indicus* methanol extract (3 g) and one part of *Garcinia mangostana* methanol extract (1 g)

Example 17

Process for Preparing Compositions 2A, 2B and 2C:

Composition 2A: Composition 2A was prepared by mixing unit doses of the following components:
Two parts of *Sphaeranthus indicus* ethyl acetate extract (2 g) and
One part of *Garcinia mangostana* methanol extract (1 g)
Composition 2B: Composition 2B was prepared by mixing unit doses of the following components:
One part of *Sphaeranthus indicus* ethyl acetate extract (1 g) and
Two parts of *Garcinia mangostana* methanol extract (2 g)
Composition 2C: Composition 2C was prepared by mixing unit doses of the following components:
One part of *Sphaeranthus indicus* ethyl acetate extract (1 g) and
One part of *Garcinia mangostana* methanol extract (1 g)

Example 13

Assessment of Pro-Lipolytic Activity of *Sphaeranthus Indicus* Ethyl Acetate Extract (LI/DD-II/054A/01) and 7-hydroxyfrullanolide (LI054A01) in Differentiated Adipocytes:

The lipolytic activity was assessed in mature adipocytes as per the procedure of Chemicon International, USA, by measuring free glycerol secreted into the culture medium. One hundred thousand 3T3-L1 Human pre-adipocyte cells in Dulbecco's Modified Eagles Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium containing 10 μg/ml insulin, 1.0 μM dexamethasone, and 0.5 mM isobutylmethylxanthine (IBMX). The cells were differentiated for 5 days and then the culture medium was removed. The monolayer was washed twice with wash solution (Hank's balanced salt solution), and then 250 μL of incubation solution (Hank's balanced salt solution plus 2% bovine serum albumin) was added to the wells in triplicate in presence or absence of *Sphaeranthus indicus* ethyl acetate extract (LI/DD-II/054A/01) and 7-hydroxyfrullanolide (LI054A01), and the cells were further incubated for 16 h. To measure lipolysis, 200 μL of free glycerol assay reagent was added to 25 μL of culture supernatants and controls containing glycerol standard. The samples and the controls were incubated for 15 min, and the absorbance was read at 540 nm. A standard curve constructed from the glycerol was used to calculate the concentration of free glycerol in the culture supernatants. The percentage increase in glycerol concentration in the sample solutions compared to the control containing the known concentrations of glycerol corresponds to the percentage acceleration of lipolysis by LI/DD-II/054A/01 or LI054A01. The percentage increase in lipolysis accelerated by LI/DD-II/054A/01 and LI054A01 are summarized table II.

Pro-Lipolytic Activity of *Sphaeranthus indicus*

TABLE II

| S. No | Name of the product | % acceleration of lipolysis |
|---|---|---|
| 1 | LI/DD-II/054A/01 | 26.7% at 25 μg/ml |
| 2 | LI054A01 | 47.8% at 5 μg/ml |

We claim:

1. A method of increasing energy and/or mental alertness in a subject suffering from stress, fatigue, and/or obesity, comprising orally administering a biologically active composition to the subject, said biologically active composition comprising an effective amount of:
    an organic or aqueous organic solvent extract of *Sphaeranthus indicus*, said solvent extract of *Sphaeranthus indicus* containing from 5% to 21% 7-hydroxyfrullanolide.

2. The method of claim 1, wherein the biologically active composition further comprises:
    at least one biologically active ingredient selected from the group consisting of extracts of *Garcinia mangostana* fruit rind, *Osmium basilicum*, *Zingiber officinalis*, *Tribulus terrestris*, vitamins, amino acids, taurine, an extract of *Ginkgo biloba*, *Rhodiola* and an extract of guarana,
    said composition optionally containing an excipient, diluent or carrier.

3. The method of claim 1, wherein the biologically active composition further comprises:
    an extract of *Garcinia mangostana* fruit rind comprising an effective amount of α-mangostin, γ-mangostin, or a mixture thereof; and
    at least one excipient, diluent or carrier.

4. The method of claim 1, wherein said solvent extract of *Sphaeranthus indicus* is obtained by extraction of at least one plant part selected from the group consisting of leaves, flower heads, stem, root, whole plant, and mixtures thereof.

5. The method of claim 1, wherein the solvent extract of *Sphaeranthus indicus* is selected from the group consisting of a C1 to C5 alcoholic solvent extract, a C1 to C7 hydrocarbon solvent extract, an ester solvent extract, a dichloromethane extract, a chloroform extract, an acetone extract, a methyl isobutyl ketone extract, and mixtures thereof.

6. The method of claim 1, wherein said biologically active composition is formulated into a dietary supplement, food ingredient, beverage, snack or energy drink.

7. The method of claim 1, wherein said organic solvent extract of *Sphaeranthus indicus* is obtained by extraction of flower heads.

8. A method of increasing energy and/or mental alertness in a subject suffering from stress, fatigue and/or obesity, comprising orally administering a biologically active composition to the subject said biologically active composition comprising an effective amount of:
an organic solvent extract of *Sphaeranthus indicus* comprising an effective amount of at least one frullanolide or eudesmanoid sesquiterpene compound, said organic solvent extract of *Sphaeranthus indicus* being selected from the group consisting of a C1 to C5 alcoholic solvent extract, a C1 to C7 hydrocarbon solvent extract, an ester solvent extract, a dichloromethane extract, a chloroform extract, an acetone extract, a methyl isobutyl ketone extract, and mixtures thereof.

9. The method of claim 8, wherein the biologically active composition further comprises:
at least one biologically active ingredient selected from the group consisting of extracts of *Garcinia mangostana* fruit rind, *Osmium basilicum, Zingiber officinalis, Tribulus terrestris*, vitamins, amino acids, taurine, an extract of *Ginkgo biloba, Rhodiola* and an extract of guarana,
said composition optionally containing an excipient, diluent or carrier.

10. The method of claim 8, wherein the biologically active composition further comprises:
an extract of *Garcinia mangostana* fruit rind comprising an effective amount of α-mangostin, γ-mangostin, or a mixture thereof; and
at least one excipient, diluent or carrier.

11. The method of claim 8, wherein said at least one frullanolide or eudesmanoid sesquiterpene compound is selected from the group consisting of 7-hydroxyfrullanolide; 11α,13-dihydro-3α,7α-dihydroxy-4,5-epoxy-6β,7-eudesmanolide; 11β,13-dihydro-7α-acetoxy-3β-hydroxy-6β,7-eudesm-4-enolide; 3-keto-β-eudesmol; 11α,13-dihydro-3α,7α-dihydroxyeudesm-4-en-6α,12-olide; 11α,13-dihydro-3α,7α-dihydroxyfrullanolide; 11α,13-dihydro-7α,13-dihydroxyfrullanolide; 11α,13-dihydro-7α-hydroxy-13-methaoxyfrullanolide; 2α,7α-dihydroxy-4-en-11,13-dihydroeudesm-6,12-olide; 2α-hydroxycostic acid; 3-keto-7α-hydroxyeudesm-4-en-6,12-olide (cryptomeridiol); 4-epicryptomeridiol; sphaeranthanolide; 2α-hydroxysphaerantholide; 2α-acetoxysphaerantholide; 2α,7α-dihydroxysphaerantholide; 2α-acetoxy-7α-hydroxysphaerantholide and 2α-acetoxy-5α-hydroxyisosphaerantholide and mixtures thereof.

12. The method of claim 8, wherein the effective amount of at least one frullanolide or eudesmanoid sesquiterpene compound is between 0.01% and 99.99%.

13. The method of claim 12, wherein the effective amount of at least one frullanolide or eudesmanoid sesquiterpene compound is between 0.01% and 95%.

14. The method of claim 13, wherein the effective amount of at least one frullanolide or eudesmanoid sesquiterpene compound is between 5% and 21%.

15. The method of claim 8, wherein said biologically active composition is formulated into a dietary supplement, food ingredient, beverage, snack or energy drink.

16. The method of claim 8, wherein said biologically active composition further comprises:
an organic or aqueous organic solvent extract of *Sphaeranthus indicus*, said solvent extract of *Sphaeranthus indicus* containing from 5% to 21% 7-hydroxyfrullanolide.

17. The method of claim 8, wherein said organic solvent extract of *Sphaeranthus indicus* is obtained by extraction of flower heads.

* * * * *